(12) United States Patent
Doyle

(10) Patent No.: US 12,090,208 B2
(45) Date of Patent: *Sep. 17, 2024

(54) PEPTIDE DRUG IMPROVEMENT USING VITAMIN $B_{12}$ AND HAPTOCORRIN BINDING SUBSTRATE CONJUGATES

(71) Applicant: Robert Doyle, Manlius, NY (US)

(72) Inventor: Robert Doyle, Manlius, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/558,920

(22) Filed: Dec. 22, 2021

(65) Prior Publication Data

US 2022/0184218 A1 Jun. 16, 2022

Related U.S. Application Data

(63) Continuation of application No. 16/093,422, filed as application No. PCT/EP2017/027625 on Apr. 14, 2017, now Pat. No. 11,207,415.

(51) Int. Cl.
| | |
|---|---|
| *A61K 47/54* | (2017.01) |
| *A61K 9/00* | (2006.01) |
| *A61K 38/26* | (2006.01) |
| *A61K 47/64* | (2017.01) |

(52) U.S. Cl.
CPC .......... *A61K 47/549* (2017.08); *A61K 9/0019* (2013.01); *A61K 38/26* (2013.01); *A61K 47/64* (2017.08)

(58) Field of Classification Search
CPC .............................. A61K 47/551; A61K 38/00
See application file for complete search history.

(56) References Cited

U.S. PATENT DOCUMENTS

| | | | | |
|---|---|---|---|---|
| 11,207,415 B2 * | 12/2021 | Doyle | ..................... | A61K 38/26 |
| 2013/0344620 A1 * | 12/2013 | O'Farrell | ............... | G01N 33/84 |
| | | | | 530/391.1 |

FOREIGN PATENT DOCUMENTS

WO WO-2006009874 A2 * 1/2006 ............. A61K 31/70

OTHER PUBLICATIONS

Hippe et al. "Nature of vitamin B12 binding: II. Steric orientation of vitamin B12 on binding and number of combining sites of human intrinsic factor and the transcobalamins", Biochimica et Biophysica Acta (BBA)—Protein Structure vol. 243, Issue 1, Jul. 25, 1971, pp. 75-82 (Year: 1971).*
Borner et al., "Corrination of a GLP-1 Receptor Agonist for Glycemic Control without Emesis", Cell Reports, 2020, 25 pages. (Year: 2020).*
Hippe et al., "Nature of Vitamin B12 Binding, II: Steric Orientation of Vitamin B12 on Binding and Number of Combining Sites of Human Intrinsic Factor and the Transcobalamins", Biochimica Et Biophysica Acta, 1971, 75-82. (Year: 1971).*

* cited by examiner

*Primary Examiner* — Lianko G Garyu
(74) *Attorney, Agent, or Firm* — David L. Nocilly; Bond Schoeneck & King PLLC

(57) ABSTRACT

The invention involves the coupling of compounds that can be bound by Haptocorrin (R-binder; Transcobalamin I; HC) to a target drug to improve pharmacokinetics, avoid undesirable side effects, and/or modify CNS access and localization. The pharmaceutical effect may be improved by conjugating the drug to haptocorrin binding substrate. This allows the conjugate to become bound to unsaturated haptocorrin in the blood, thereby protecting the drug from metabolism or excretion to increase protein half-life while not interfering with the efficacy of the protein drug. The conjugation may additionally prevent the drug from reaching the central nervous system or modify where the drug localizes and produces undesirable side effects such as nausea or hypophagia. Such a route also would prevent, in all case save for actual vitamin $B_{12}$, binding by serum transcobalamin II (TCII), and thus not cause $B_{12}$ deficiency with long term use.

12 Claims, 25 Drawing Sheets

PEPTIDE DRUG IMPROVEMENT USING VITAMIN $B_{12}$ AND HAPTOCORRIN BINDING SUBSTRATE CONJUGATES

CROSS-REFERENCE TO RELATED APPLICATIONS

The present application is a continuation of U.S. application Ser. No. 16/093,422, filed on Oct. 12, 2018 as a national stage of PCT Application No. PCT/US17/27625 having an international filing date of Apr. 14, 2017 and a claim of priority to U.S. Provisional Application 62/323,013, filed on Apr. 15, 2016, and U.S. Provisional Application No. 62/372,605, filed on Aug. 9, 2016.

BACKGROUND OF THE INVENTION

1. Field of the Invention

The present invention relates to drug improvement mechanisms and, more specifically, to the improvement of protein drug pharmaceutical effects using substrates bound by haptocorrin (including vitamin B12) based compounds.

2. Description of the Related Art

One of the greatest challenges to the use of peptide drugs is the instability of peptides in serum due to the action of proteases. The ability to increase the half-life of a peptide drug in human serum is therefore often critical for successful use. Thus, improved pharmacokinetics is a major road-block in peptide drug development. Some approaches to improving pharmacokinetics by protecting a protein against degradation or excretion are based on conjugation to albumin binding proteins. Other approaches involve the use of protein binding moieties that will protect a pro-drug from degradation and release it in the blood. These approaches often inhibit the efficacy of the drug and rely on subsequent activities to release the drug before it can effective. Another challenge to the use of drugs is the prospects of side effects and, more particular, unintended central nervous system side effects. For example, the highly potent natural peptide agonist ($EC_{50}$~30 pM) of the GLP-1 receptor (GLP1-R) known as GLP1-R is rapidly degraded (half-life of two minutes) and did not translate as an effective therapeutic for the treatment of diabetes mellitus. A GLP1-R agonist form, termed Exendin-4 in its natural form and exenatide in a synthetic form (available as Byetta® from the Novo Nordisk Group) has a greater in vivo half-life (2.4 h) relative to GLP-1 and has proven to be a highly effective therapeutic used widely in the treatment of Type 2 diabetes mellitus since its approval by the FDA in 2005. However, in addition to providing the desired glucoregulation, therapeutic administration of Ex-4 is associated with unwanted weight loss (hypophagia) and chronic nausea. GLP1-R agonists in general suffer from unwanted CNS effects. Consequently, there is a need to develop an approach for improving the pharmacokinetics of peptide drugs and/or avoiding undesirable side effects.

BRIEF SUMMARY OF THE INVENTION

The invention involves the coupling of compounds that can be bound by Haptocorrin (R-binder; Transcobalamin I; HC) to a target peptide drug to improve pharmacokinetics and/or to avoid undesirable side effects, and/or to modify CNS access and localization. The pharmaceutical effect of a peptide drug may be improved by conjugating the drug to haptocorrin binding substrate including vitamin $B_{12}$, a $B_{12}$ derivative, a cobinamide (e.g., dicyanocobinamide, monoaquo-monocyano-cobinamide etc). The conjugation to certain $B_{12}$ and/or related compounds allows the conjugate to become bound to unsaturated haptocorrin in the blood, thereby protecting the drug from metabolism or excretion to increase protein half-life while not interfering with the efficacy of the protein drug. The conjugation to certain $B_{12}$ related compounds may additionally prevent the drug from reaching the central nervous system or modify where in the CNS the drug localizes and producing undesirable side effects, or produces a desired effect as a consequence of such CNS modification. Such a route also would prevent, in all case save for actual vitamin B12s (e.g., cyanocobalamin; adenosylcobalamin, aquocobalamin), binding by serum transcobalamin II (TCII). By not becoming bound to TCII, the transporter necessary for delivering B12 to proliferating cells, such conjugates would also not cause B12 deficiency with long term use—a major concern in the field with using B12 conjugates. The method of the present invention comprises providing an improvement to a pharmaceutical effect of a peptide drug by conjugating the peptide drug to a substrate bound by haptocorrin prior to administering the peptide drug to a patient. The peptide drug may be Exendin-4, amylin, PYY3-36, PYY1-36, GLP-1, Pramlintide, insulin, etc). The improvement may be a longer half-life when injected intravenously or subcutaneously and/or a reduction in CNS associated side effects as appropriate, improvement in CNS effects through modification in CNS localization etc and conducted without inducing vitamin B12 deficiency. CNS side effect improvements may comprise a reduction in nausea. CNS side effect improvements may also comprise a reduction in weight loss (hypophagia). CNS improvements may be localization in alternate regions of the brain to parent, unmodified drug, with concomitant improvements in pharmacodynamic effects of the drug for example on memory and learning, or reduction in addictive behavior etc,

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a schematic of a haptocorrin binding substrate covalently bound to a peptide drug according to the present invention; and FIG. 2 is a graph of the binding affinity of a peptide drug alone, when covalently bound to a haptocorrin binding substrate, and when bound to the haptocorrin binding compound and haptocorrin FIG. 3 is a schematic of the synthesis of $B_{12}$-Ex-4 conjugates with the following reagents and conditions: (i) EDCl, HOBt, propargyl amine, rt, DMSO, 16 h; (ii) EDCl, HOBt, 1-amino-3-butyne, rt, DMSO, 16 h; (iii) EDCl, HOBt, 1-amino-4-pentyne, rt, DMSO, 16 h; (iv) EDCl, HOBt, 1-amino-5-hexyne, rt, DMSO, 16 h; (v) (2), $CuSO_4$, sodium ascorbate, 1, Water/DMF 4:1, 1 h; (vi) (3), $CuSO_4$, sodium ascorbate, 1, Water/DMF 4:1, 1 h; (vii) (4), $CuSO_4$, sodium ascorbate, 1, Water/DMF, 4:11 h; (viii) (5), $CuSO_4$, sodium ascorbate, 1, 1 h;

FIG. 4 is an LC trace showing purified compound 7 as a monomer (7.5 min) and dimer (6.5 min) and ESI MS (inset) of compound 7 showing m/z of 1415.5 Da, which corresponds to the +4 of compound 7 yielding a consistent mass of 5658 Da;

FIG. 5 is a graph of the $EC_{50}$ curves for compounds 1, 6, 7, 8, and 9 and a plot of the $EC_{50}$ values for compounds 1, 6, 7, 8, and 9 (27, 121, 68, 246 and 271 pM, respectively);

DETAILED DESCRIPTION OF THE INVENTION

Figure 1:
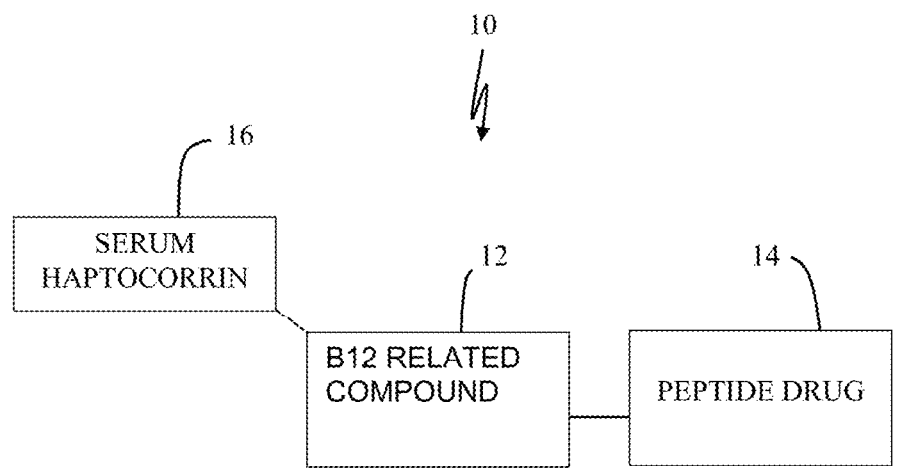

Referring to the figures, wherein like parts refer to like parts throughout, there is seen in FIG. 1 a schematic of a conjugate 10 formed by covalently binding a $B_{12}$ related compound 12, such as $B_{12}$, an analog of $B_{12}$, a derivative of $B_{12}$, or haptocorrin binding substrate based on $B_{12}$, to a peptide drug 14. As explained herein, when injected intravenously into a patient, $B_{12}$ related compound 12 of conjugate 10 can improve the pharmacokinetics of peptide drug 14 by protecting protein drug 14 against degradation while not inferring with the pharmaceutical effects of peptide drug 14. In addition, certain $B_{12}$ related compounds 12 can also inhibit peptide drug 14 inducing undesirable side effects.

Example 1

Referring to FIG. 1, the present invention may comprise the use of a haptocorrin binding substrate as $B_{12}$ related compound 12 for reducing degradation of peptide drug 14. In this example, haptocorrin binding substrate may comprise cobalamin ($B_{12}$), cyanocobalamin, dicyanocobinamide, hydroxocobalamin, methylcobalamin, adenosylcobalamin, and combinations thereof which have been modified for covalent binding to drug 14. Peptide drug 14 may comprise nesiritide, ceruletide, bentiromide, exenatide, gonadorelin, enfuvirtide, vancomycin, icatibant, secretin, leuprolide, glucagon recombinant, oxytocin, bivalirudin, sermorelin, gramicidin d, insulin recombinant, capreomycin, salmon calcitonin, vasopressin, cosyntropin, bacitracin, octreotide, abarelix, vapreotide, thymalfasin, insulin, mecasermin, cetrorelix, teriparatide, corticotropin, pramlintide. Peptide drug 14 may include anti-cancer substances, radionuclides, vitamins, anti-AIDS substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, opthalmics, prostaglandins, anti-depressants, anti-psychotic substances, anti-emetics, and imaging agents.

Figure 2:
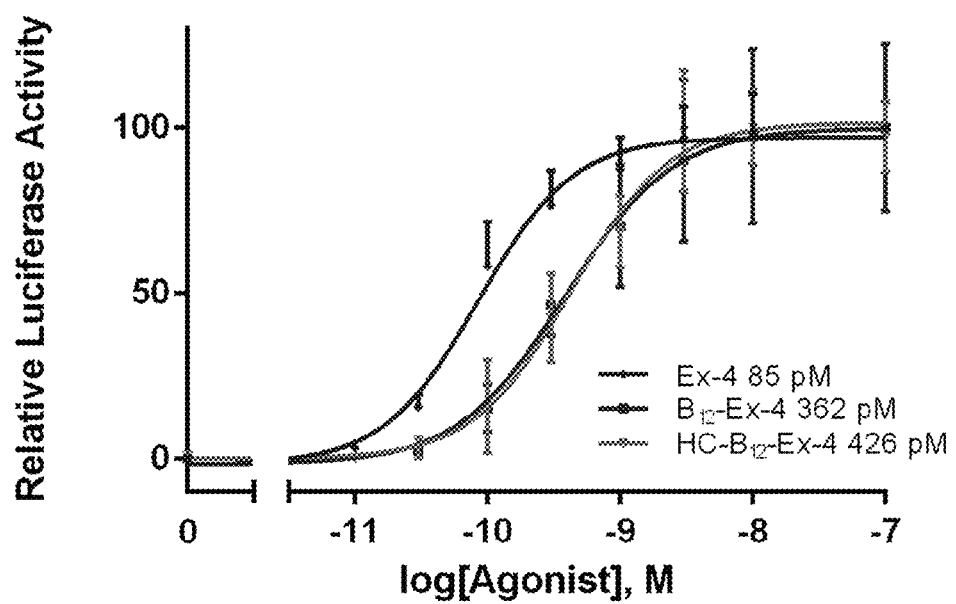

Referring to FIG. 2, binding of a potential peptide drug to haptocorrin does not adversely impact the efficacy of the drug, as measured by its affinity for the known receptor target of the drug. In the example of FIG. 2, the protein Ex-4 was evaluated for binding affinity on its own, when attached to the haptocorrin binding substrate $B_{12}$, and also when attached to $B_{12}$ and haptocorrin. Despite the covalent attachment to $B_{12}$ and non-covalent binding of the subsequent conjugate by haptocorrin, Extendin-4 continued to act as a potent agonist for its target receptor, thus establishing that the binding to haptocorrin binding substrate 12 and haptocorrin does not adversely impact the efficacy of the target drug.

With a half-life in blood of approximately 10 hours, and no known receptors in healthy cells when fully glycosylated, haptocorrin provides an exciting avenue for pharmacokinetic improvement. The unsaturated binding concentration for haptocorrin in serum is 0.3 nmol/L (compared to about 1 nmol/L for TCII in humans with 80% of $B_{12}$ and $B_{12}$ analogs bound up by HC and the remaining 20% by TCII) so, while $B_{12}$ itself would be expected to be bound up by both HC and TCII, some of the administered drug would be lost to TCII if such were used.

Example 2

Figure 3:
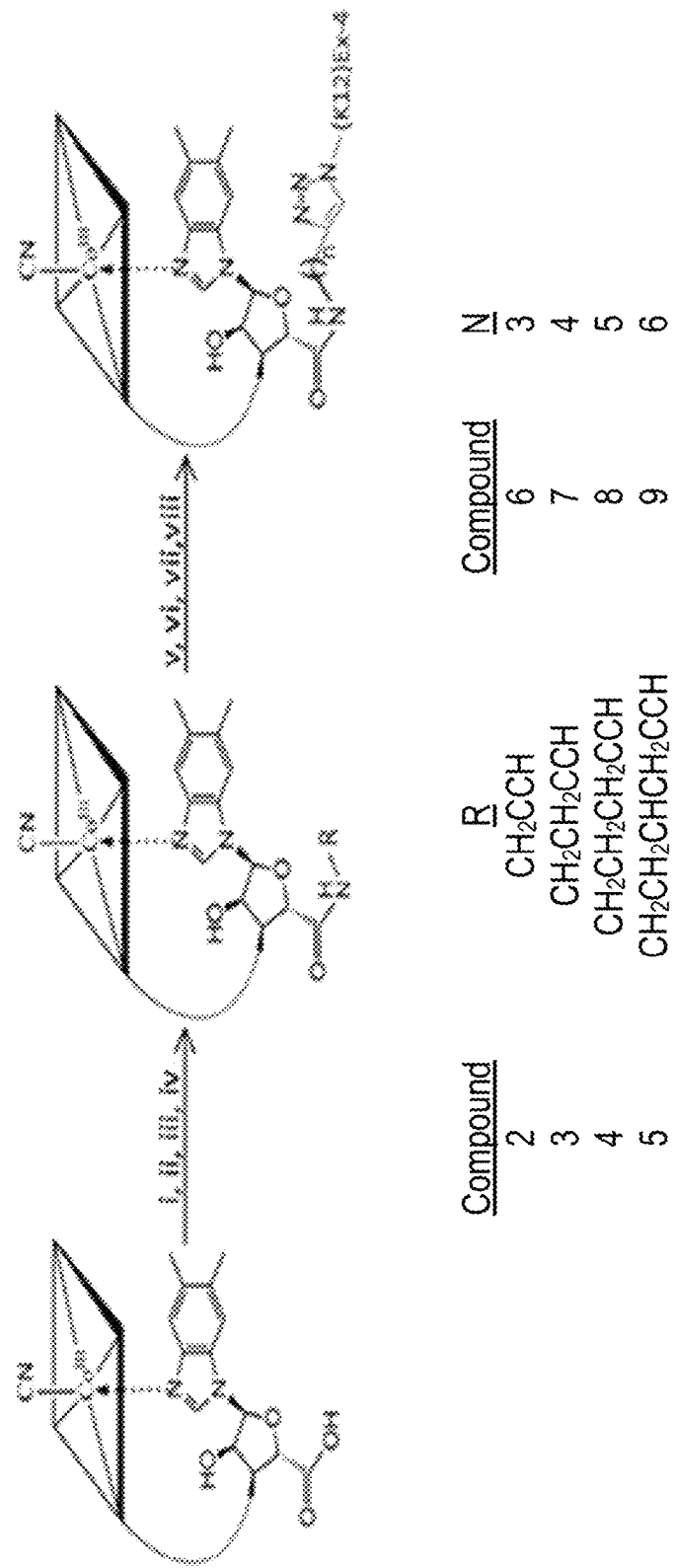

Referring to FIG. 3, the present invention may comprise the use of conjugate 10 to mitigate the side effects associated with the particular peptide drug 14 uses in conjugate. An exemplary conjugate 10 were formed using Ex-4 as peptide drug 14 and evaluated for the mitigation of side effects. Synthesis of conjugate 10 was conducted in three stages, as seen in FIG. 3. First, the 5'-hydroxyl group of $B_{12}$ was converted to a carboxylic acid using 2-iodoxybenzoic acid. The second step required reaction with a bifunctional amine-alkyne of variable methylene (n) spacer length (n=1-4). The third step involved reaction of the final '$B_{12}$-alkyne' compound with Ex-4 modified at the lysine 12 (K12) position with an ε-azido group (compound 1).

Synthesis of compound 3 using 1-amino-3-butyne as the bifunctional linker has been reported. The present invention used the latter chemistry, modified for the synthesis of compounds 2, 4, and 5, through use of either propargylamine (compound 2), 1-amino-4-pentyne (compound 4), or 1-amino-5-hexyne (compound 5), respectively. Briefly, the $B_{12}$ modified 5'-carboxylic acid was reacted with each linker in the presence of 1-ethyl-3-[3-dimethylaminopropyl]carbodiimide hydrochloride (EDCl) and hydroxybenzotriazole (HOBt) in dry DMSO at room temperature overnight, with greater than 95% isolated yields in all cases, as seen in FIG. 3. Compound 1 was then conjugated to $B_{12}$ using copper-catalyzed alkyne-azide cycloaddition (CuAAC). This conjugation was achieved by dissolving compound 1 with either compounds 2-5, respectively with copper (II) sulfate and sodium ascorbate in water/DMF (4:1) and stirring for 1 h. The reaction yields were greater than 90% with isolated purity greater than 95% for compounds 6-9 as indicated by HPLC in all cases, as seen in FIGS. 1 and 2.

Figure 4:
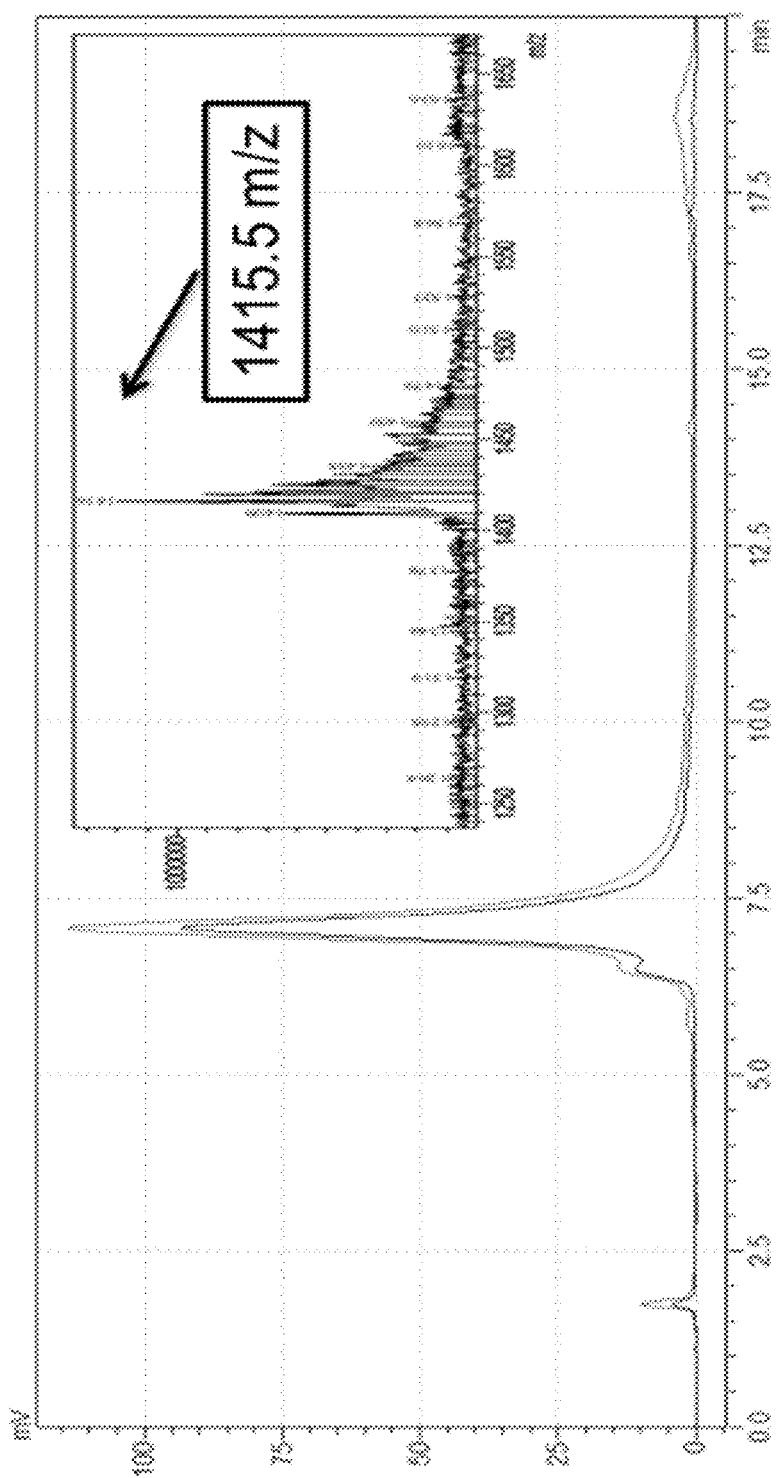

Compounds 2-5 were purified by RP-HPLC using a C18 column monitoring at 360 nm. A mobile phase of 0.1% TFA water was used with a flow rate of 1 mL/min and a gradient of 0-13% acetonitrile over 13 minutes. Compounds 2-5 were then characterized by $^1$H NMR and matrix-assisted laser desorption ionization time-of-flight mass spectrometry (MALDI-Tof MS). As seen in FIG. 4, compounds 6-9 were separated from compound 1 and unreacted $B_{12}$ on a C18 column monitored at both 280 and 360 nm. A mobile phase of 0.1% TFA water was used with a flow rate of 1 mL/min and a gradient from 20-42.5% acetonitrile for 3 min then 42.5-47% acetonitrile for 12 min. Isolated conjugates 6-9 were confirmed by electrospray mass spectrometry (ESMS) with that of compound 7 shown as representative in inset in FIG. 4. Note that the small shoulder on the front side of the LC trace was also found to be consistent with the target conjugate (compounds 6-9) and is consistent with the known tendency of Ex-4 to partially aggregate. Synthesis of compounds 6-9 was achieved in high yield (>90%) with greater than 95% purity in each case. It appears from FIG. 3 there is an obvious optimum spacer distance, with the shortest and longer distances resulting in reduced GLP-1R agonism. It is possible that interactions with the peptide, structural modification of the peptide or indeed interference with receptor interactions are all at-play (an NMR investigation study is-going and will be reported in due course). The data demonstrates the necessity of screening $B_{12}$ peptide conjugates prior to full in vivo investigations.

Each conjugate 10 was analyzed for function at the GLP-1R using Hek-GLP-1R cells incorporating a genetically-encoded FRET reporter, AKAR3. Upon binding of the GLP-1R, cAMP production is up regulated, which in turn activates protein kinase (PKA). PKA phosphorylation of AKAR3 results in a decrease of 485/535 nm emission FRET ratio. The most potent conjugate compound 7 had an $EC_{50}$ of 68 pM followed by compounds 6, 8, and 9, which had $EC_{50}$'s of 121, 246 and 405 pM, respectively.

Figure 5:
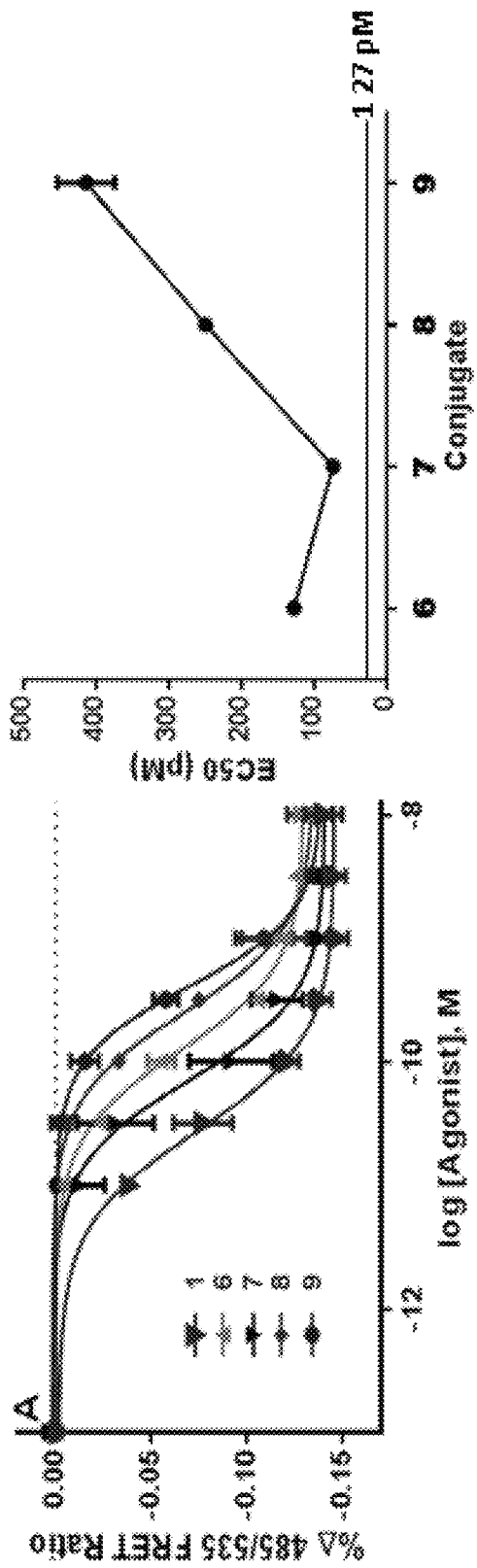
Figure 6:
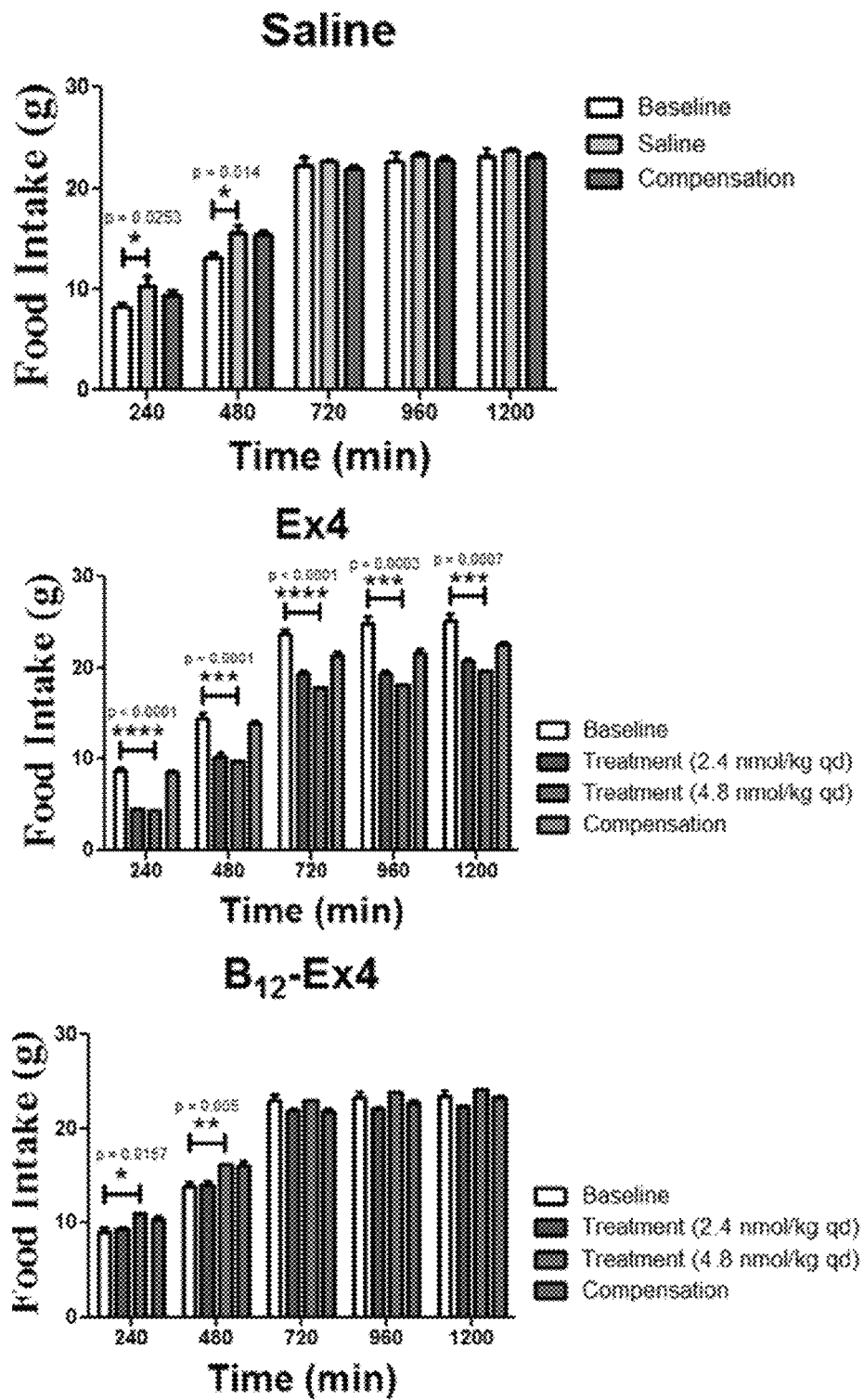
FIG. 6 is a series of graphs of food intake in male rats when given saline, Ex-4, and $B_{12}$-Ex-4.
Figure 7:
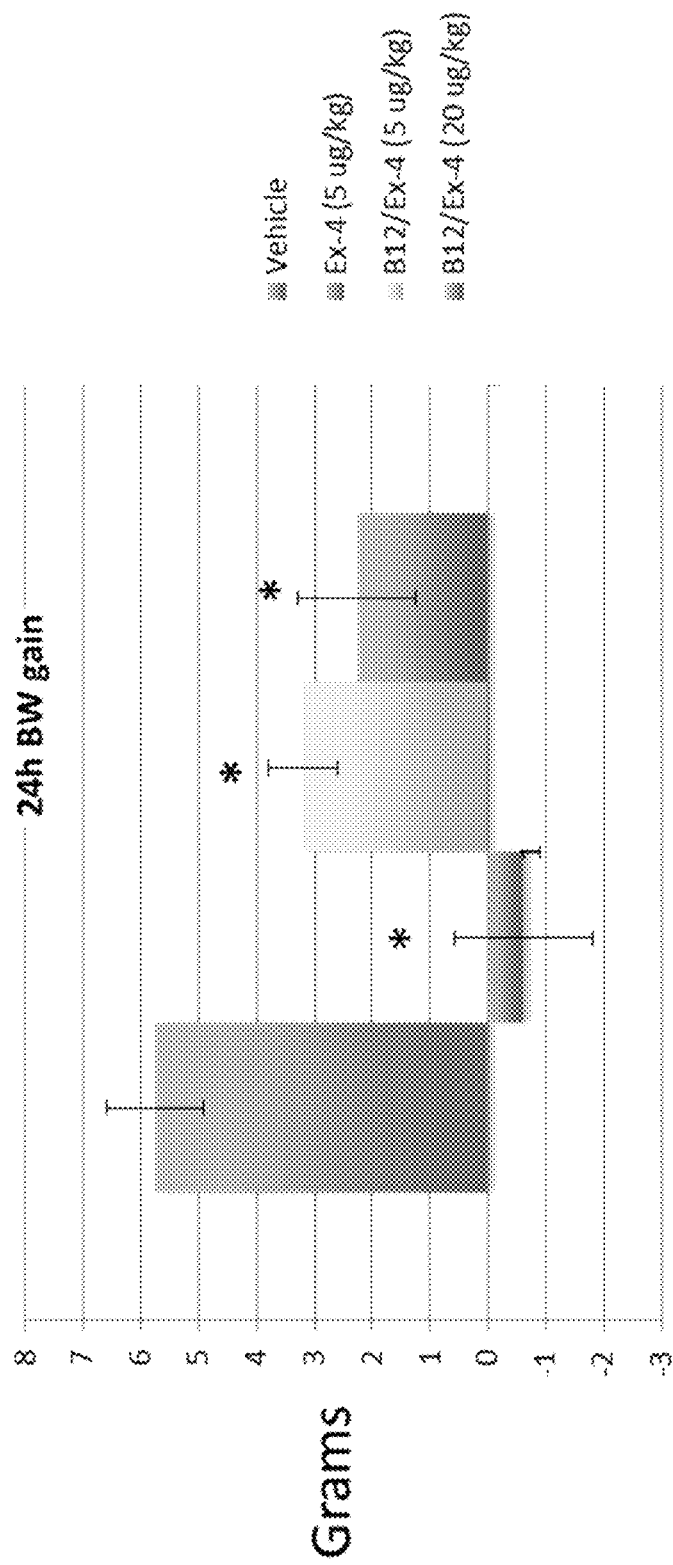
FIG. 7 is a chart of weight gain in male rats when given Ex-4 and $B_{12}$-Ex-4.
Figure 8:
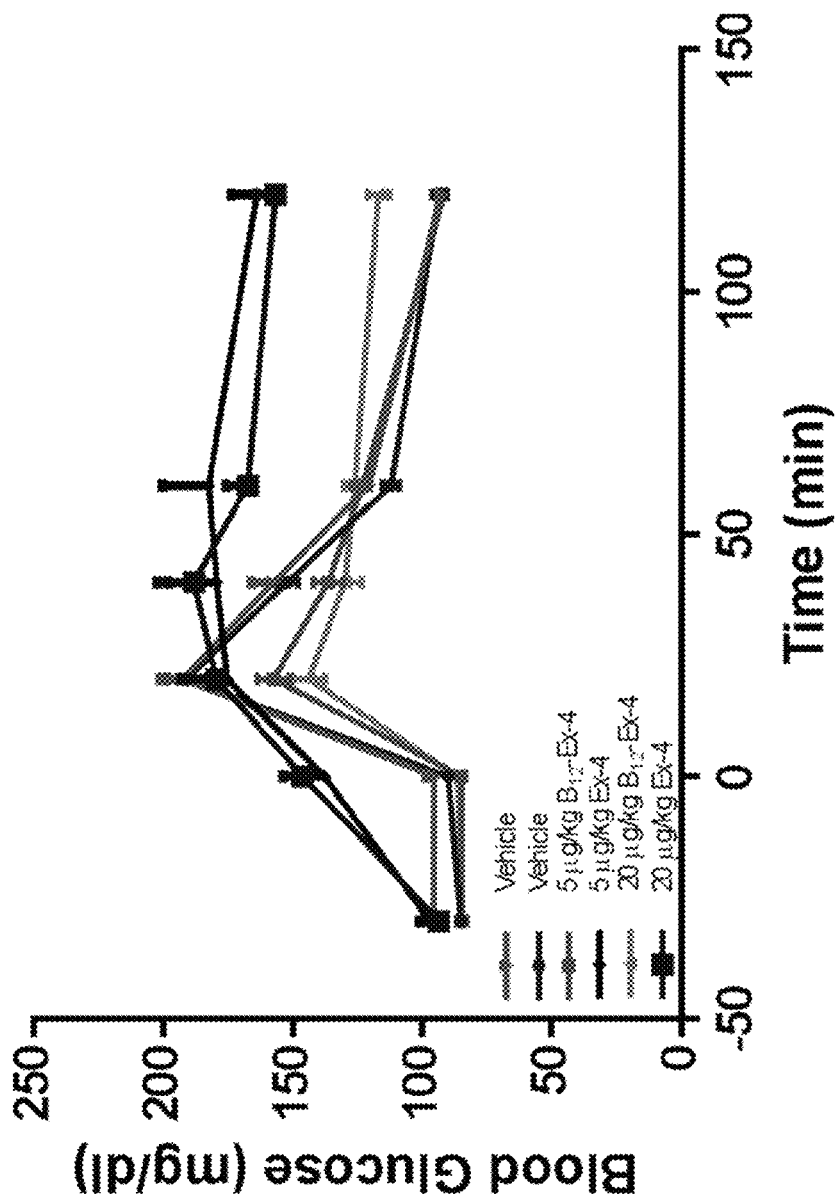
FIG. 8 is a chart of blood glucose levels in male rates when given Ex-4 and $B_{12}$-Ex-4.
Figure 9:
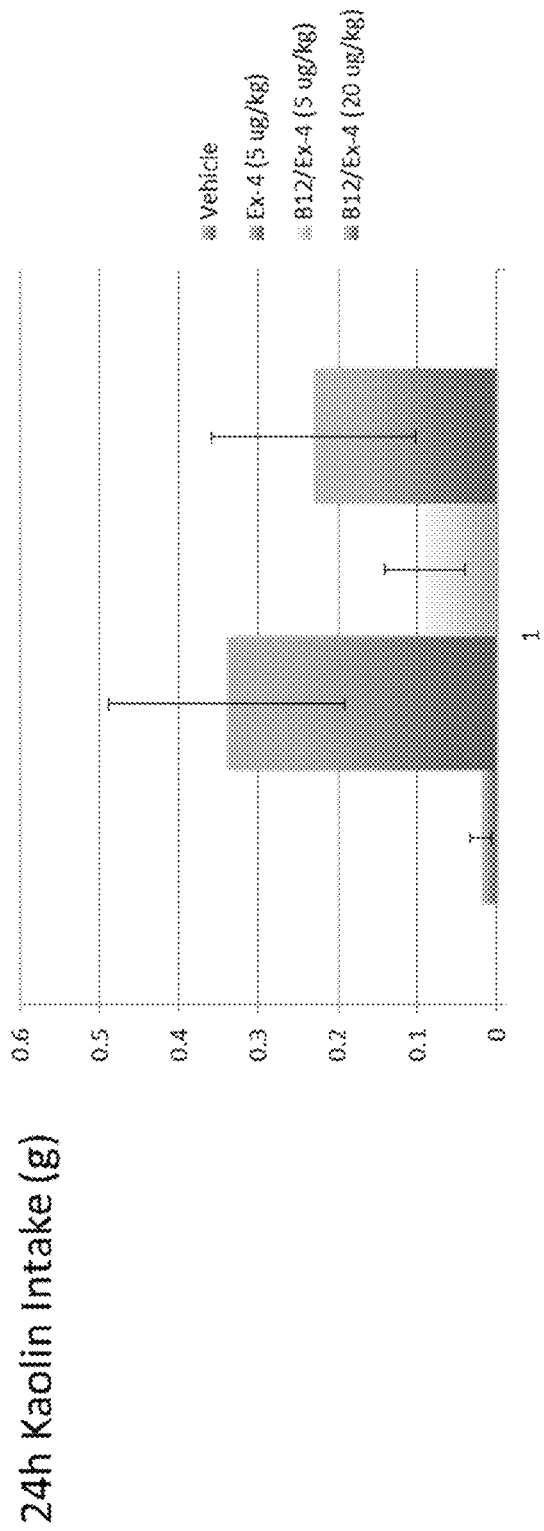
FIG. 9 is a chart of kaolin intake in male rats given Ex-4 and $B_{12}$-Ex-4.
Figure 10:
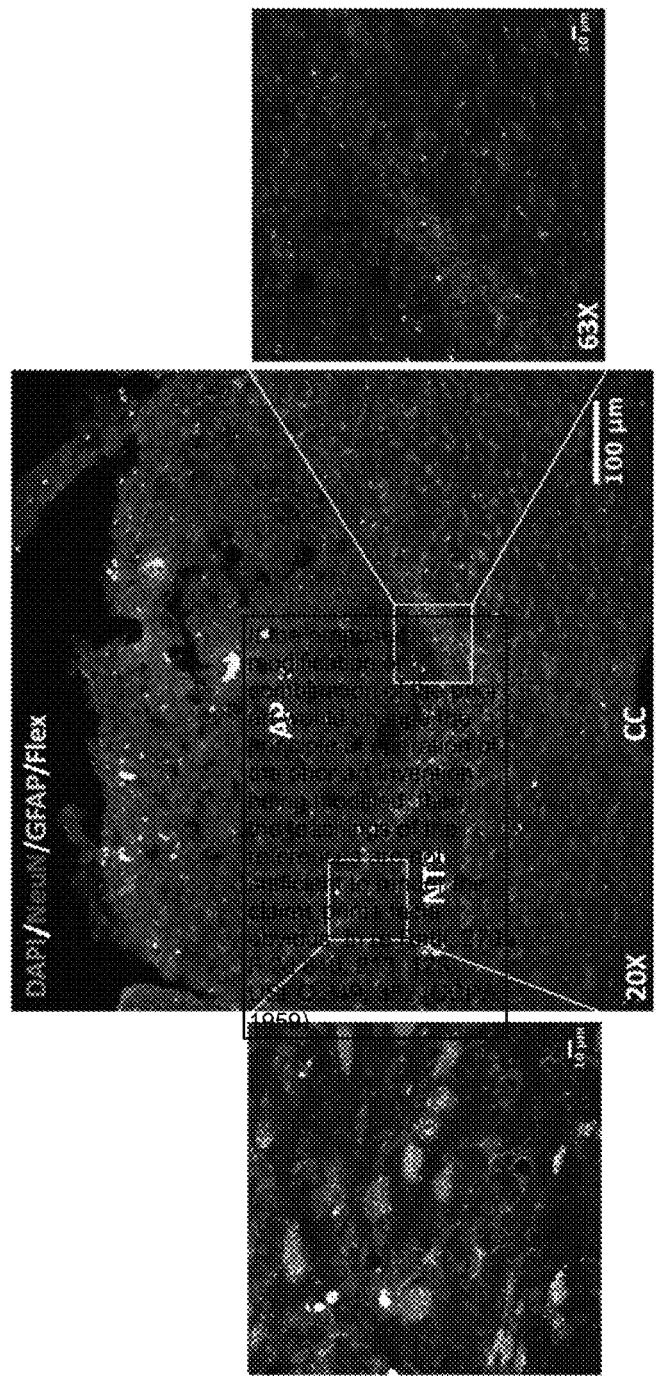
FIG. 10 is an image of fluorescently labelled exendin-4 and the dorsal vagal complex of a rat three hours after treatment.
Figure 11:
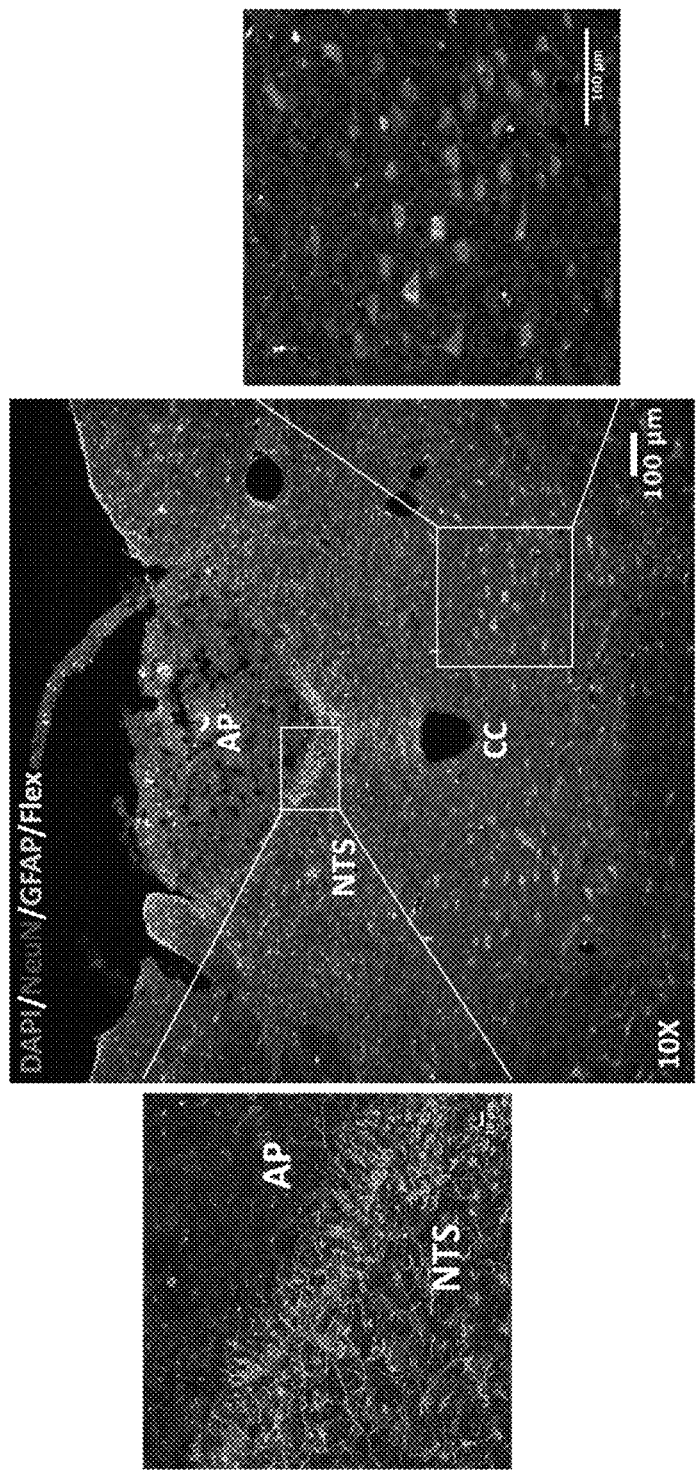
FIG. 11 is a second image of fluorescently labelled exendin-4 and the dorsal vagal complex of a rat three hours after treatment.
Figure 12:
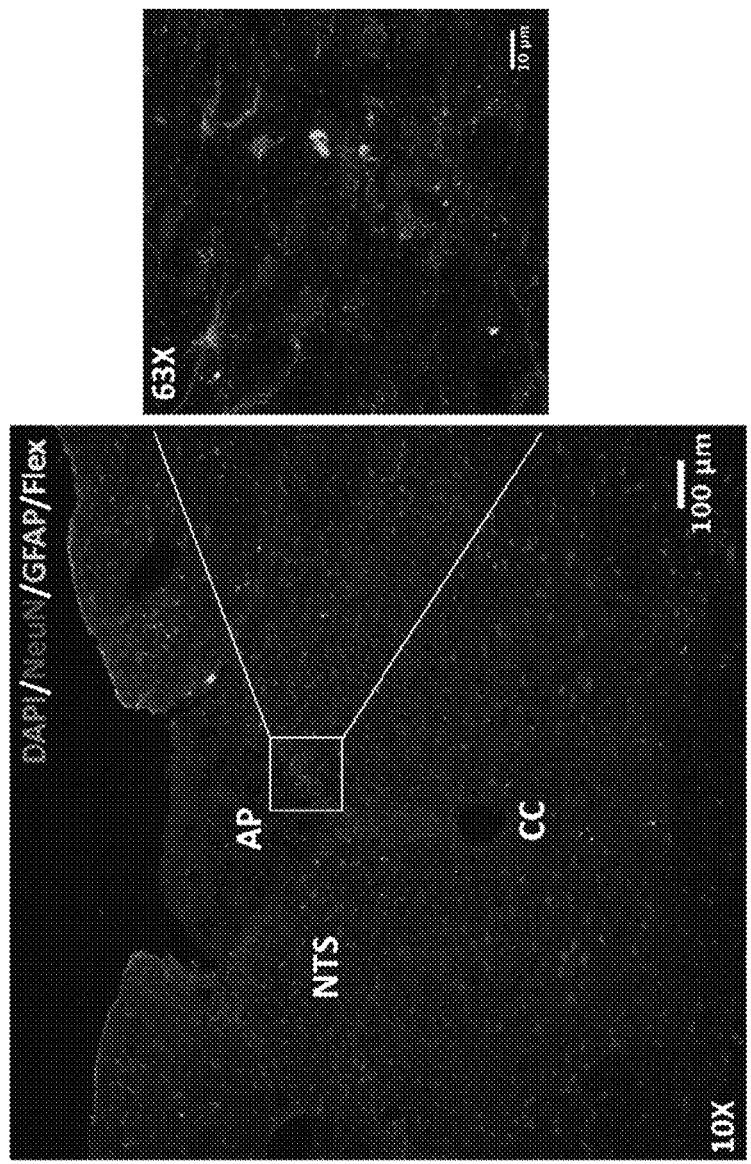
FIG. 12 is an image of fluorescently labelled exendin-4 and the dorsal vagal complex of a rat six hours after treatment.
Figure 13:
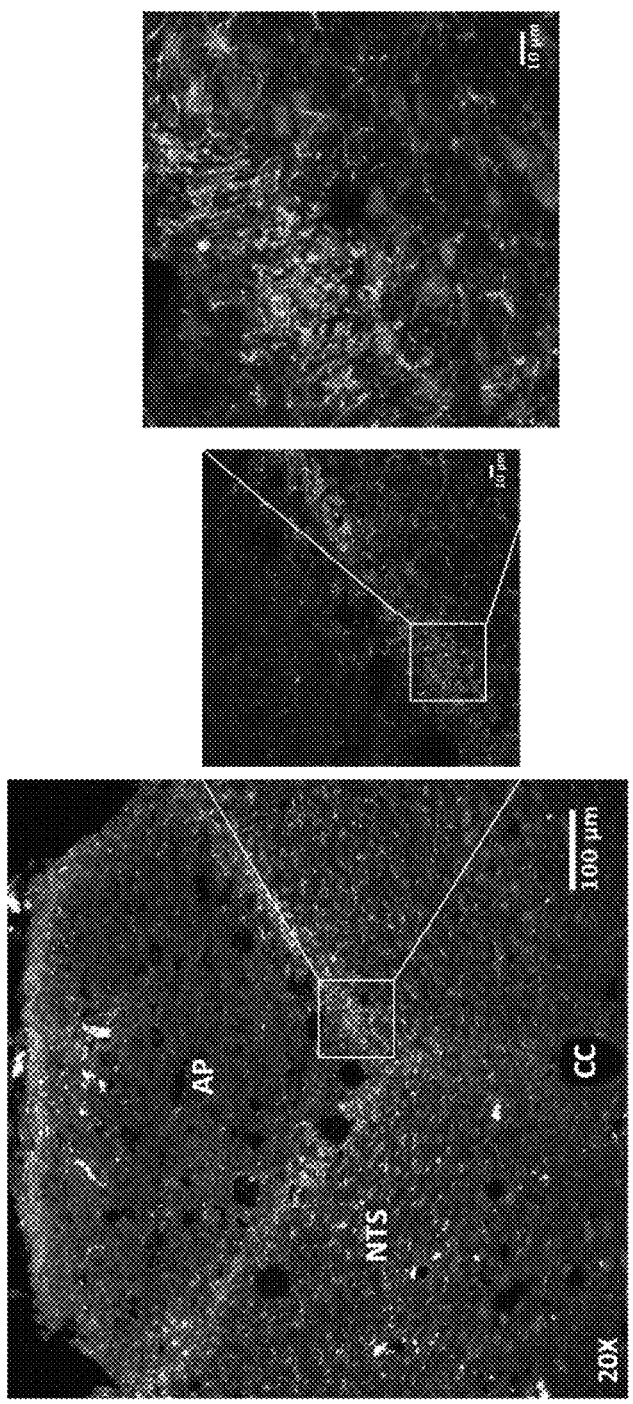
FIG. 13 is a second image of fluorescently labelled exendin-4 and the dorsal vagal complex of a rat six hours after treatment.
Figure 14:
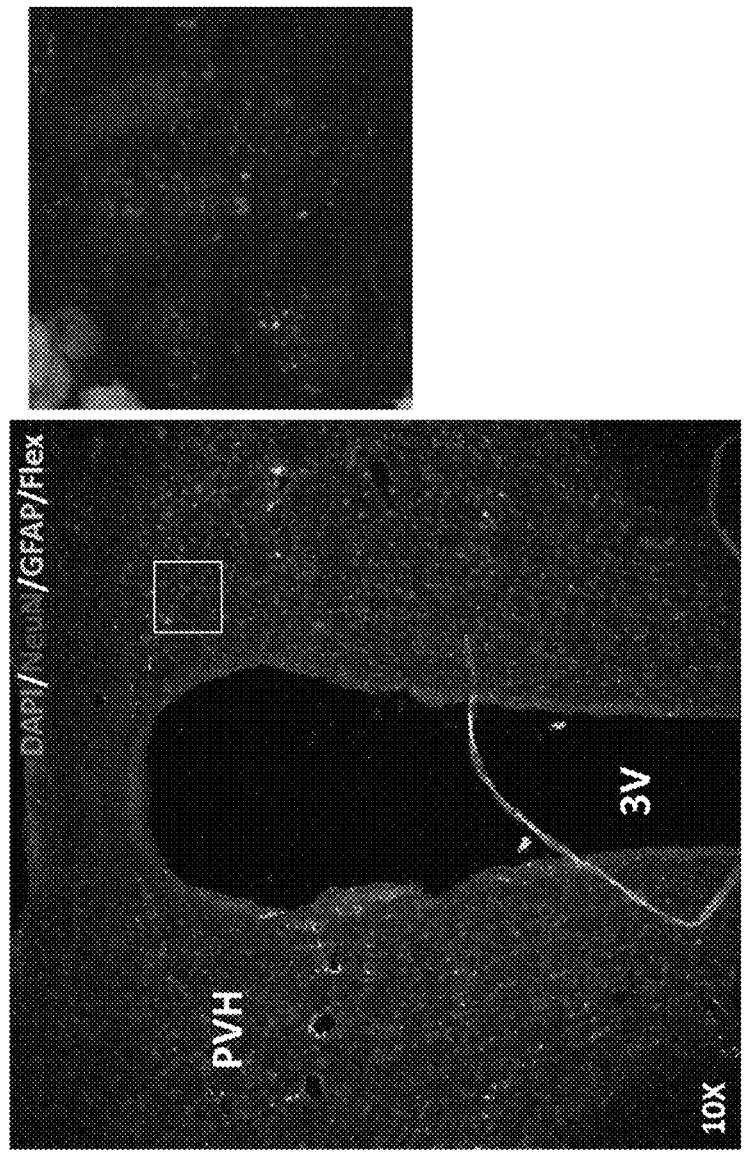
FIG. 14 is an image of fluorescently labelled exendin-4 and the paraventricular nucleus of the hypothalamus of a rat three hours after treatment.
Figure 15:
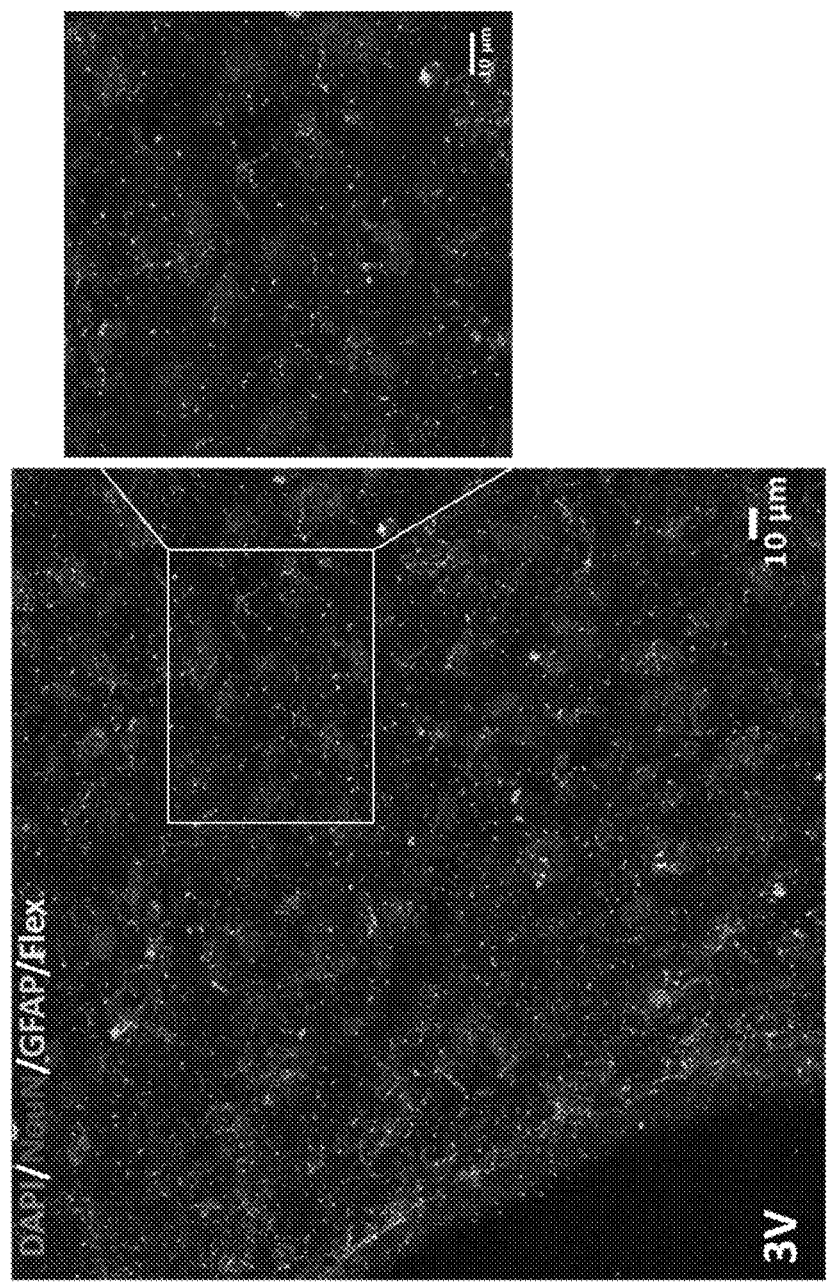
FIG. 15 is an image of fluorescently labelled exendin-4 and the paraventricular nucleus of the hypothalamus of a rat six hours after treatment.
Figure 16:
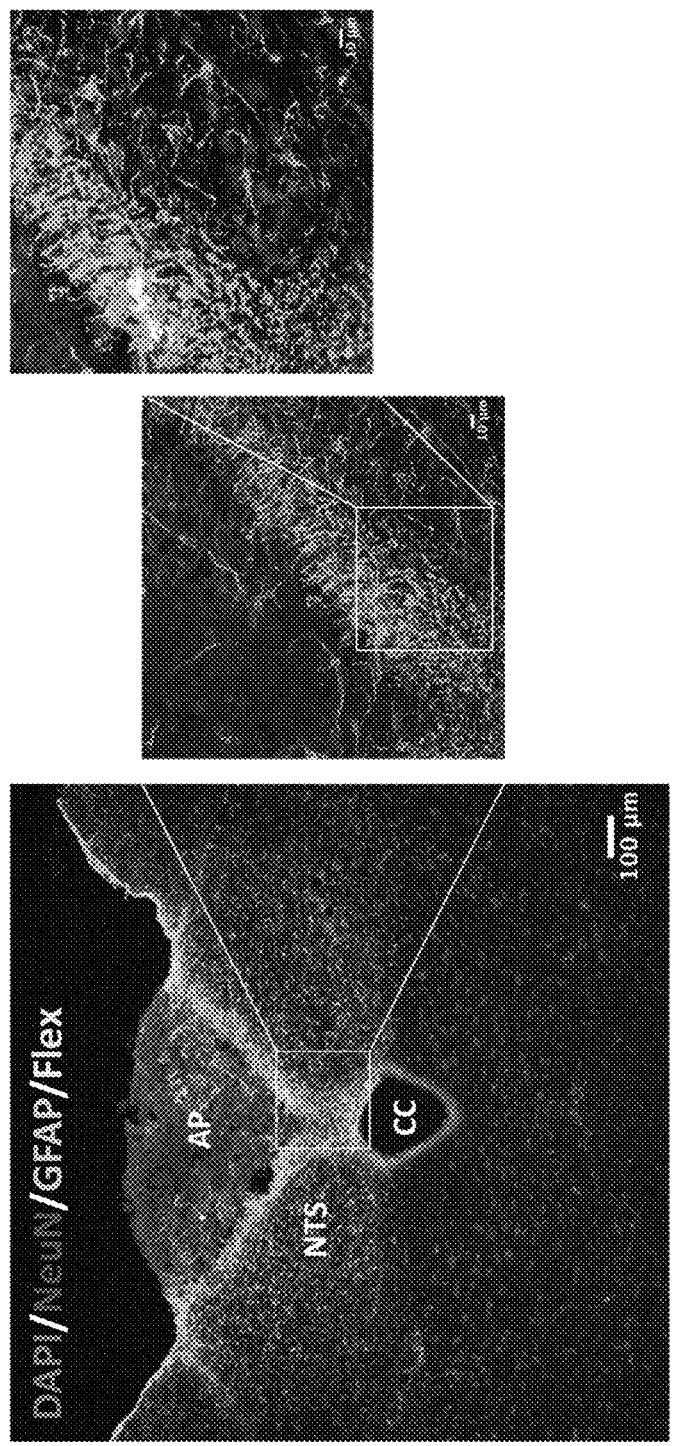
FIG. 16 is an image of a fluorescently labelled $B_{12}$ exendin-4 conjugate according to the present invention and the dorsal vagal complex of a rat three hours after treatment.
Figure 17:
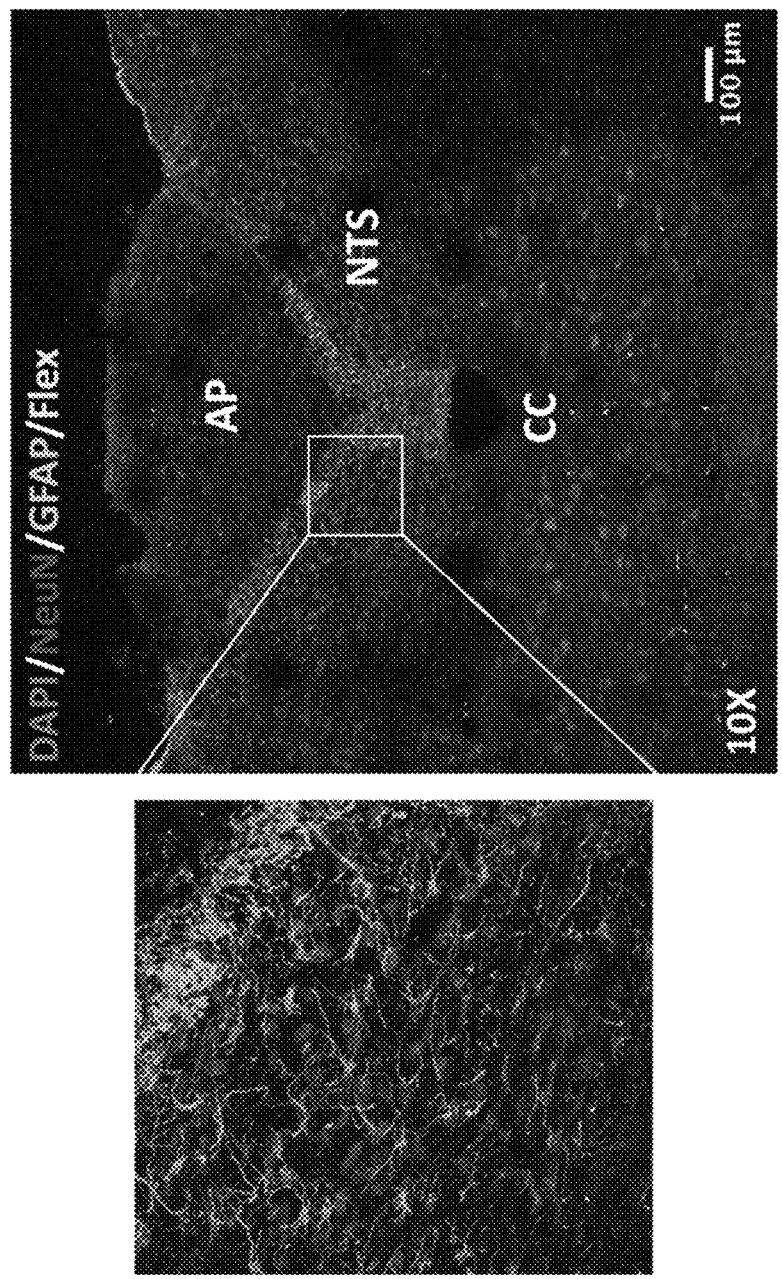
FIG. 17 is an image of a fluorescently labelled $B_{12}$ exendin-4 conjugate according to the present invention and the dorsal vagal complex of a rat six hours after treatment.
Figure 18:
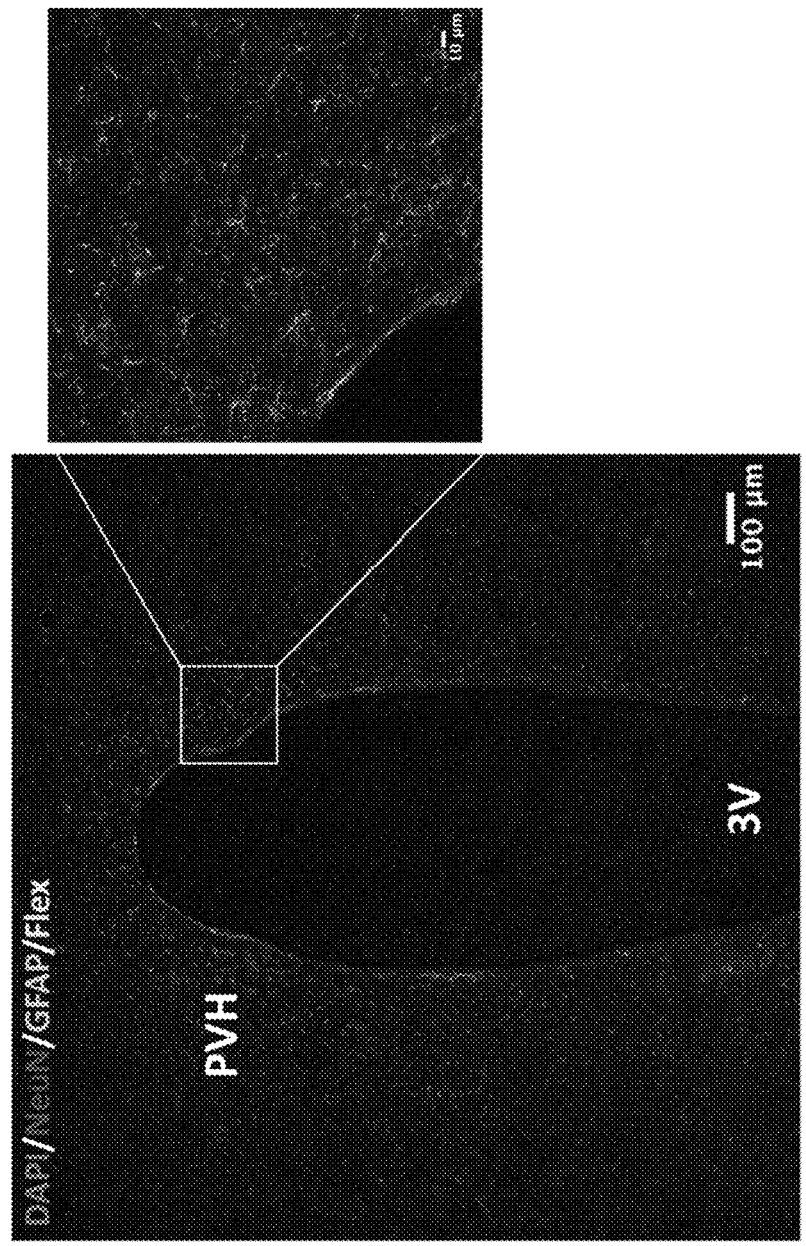
FIG. 18 is an image of a fluorescently labelled $B_{12}$ exendin-4 conjugate according to the present invention and the paraventricular nucleus of the hypothalamus of a rat three hours after treatment.
Figure 19:
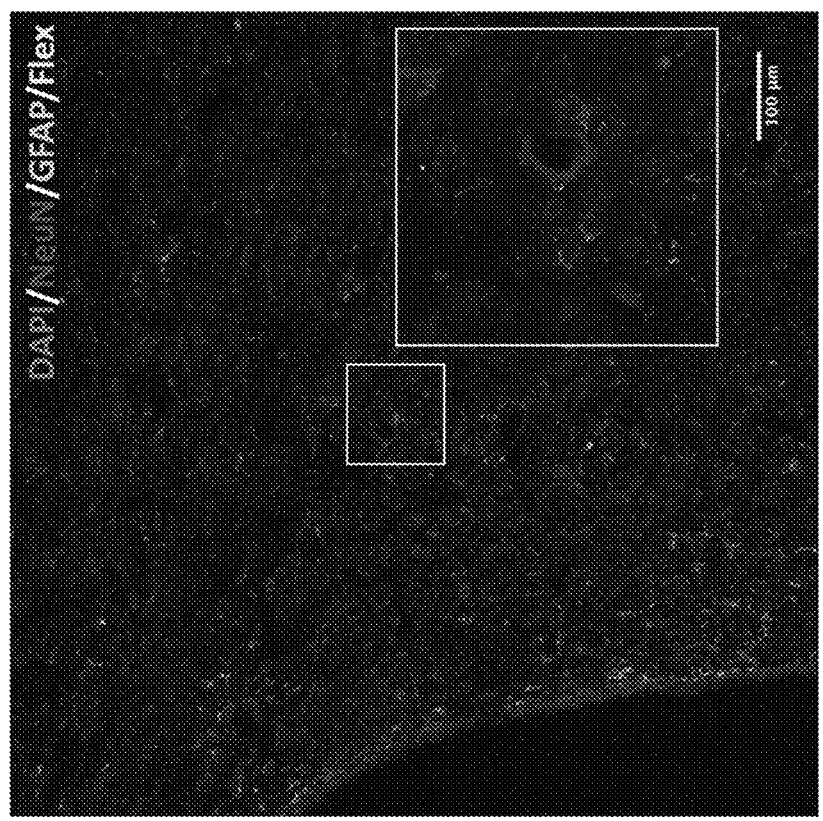
FIG. 19 is an image of a fluorescently labelled $B_{12}$ exendin-4 conjugate according to the present invention and the paraventricular nucleus of the hypothalamus of a rat six hours after treatment.

Conjugation of $B_{12}$ to Ex-4 was postulated as modifying brain uptake or localization with the effect of reducing Ex-4 activity in the brain. Such a result would likely lead to a loss of the nausea seen with Ex-4, while still allowing hypoglycemic function through action at the pancreas for example. Nausea is a common side effect of such incretin hormone use and, as such, any maintaining of glucose control that also mitigates this nausea would have considerable benefit. Accordingly, a $B_{12}$-Ex-4 conjugate was evaluated for its ability to reduce side effects, such as nausea, while maintaining efficacy with respect to glucoregulation. Referring to FIG. 4, test data showed that $B_{12}$-Ex-4 no longer results in food intake reduction in male rats compared to the same concentrations as Ex-4 (positive control), and that $B_{12}$-Ex-4 produces results similar to a saline negative control. Referring to FIG. 5, even at doses 4 times that of an Ex-4 comparative control, the reduction in body weight (BW) gain associated with $B_{12}$-Ex-4 is minimal compared to vehicle control. Notably, administration of Ex-4 alone produced a significant body weight gain reduction. Referring to FIG. 6, glucose was administered orally (standard Oral Glucose tolerance test) to male rates. While Ex-4 caused hyperglycemia, $B_{12}$-Ex-4 induced a hypoglycemic response. Referring to FIG. 7, a Pica study was performed to gauge nausea. The more kaolin consumed by the animal, the greater the degree of nausea. As seen in FIG. 7, there is significantly less consumption of kaolin (indicative of reduced nausea) associated with the use of $B_{12}$-Ex-4 relative to Ex-4.

The conjugation of $B_{12}$ to Exendin-4 thus is believed to mitigate the central nervous system responses to Ex-4 in male rats, resulting in a hypoglycemic response, reduction of appetite suppression, and reduction of nausea compared to that associated with administration of Ex-4 alone. Based on these animal model studies, a $B_{12}$-Ex-4 conjugate in humans (in any and all forms) would maintain the targeted glucose regulation of Ex-4 while having reduced or eliminated nausea and appetite suppression side-effects.

The ability of $B_{12}$ related compound 12 to prevent central nervous system side effects when conjugated to peptide drug 14 was further demonstrated using images of rat brain that were administered with fluorescent Ex-4 and fluorescent $B_{12}$-Ex-4. FIGS. 10-15 demonstrate Ex-4 reaches the hypothalamus in the brain (noted as FLEX in the files for Fluorescent exendin). FIGS. 16-19 demonstrate that $B_{12}$ does not reach the hypothalamus. As the hypothalamus region of the brain has GLP1-receptors and is associated with the chronic nausea that results from the administration of Ex-4, the ability of $B_{12}$ related compound 12 to prevent peptide drug 14 from reaching the hypothalamus explains in large part why the $B_{12}$-Ex-4 conjugate reduced nausea in the rat studies.

Example 3

Figure 20:
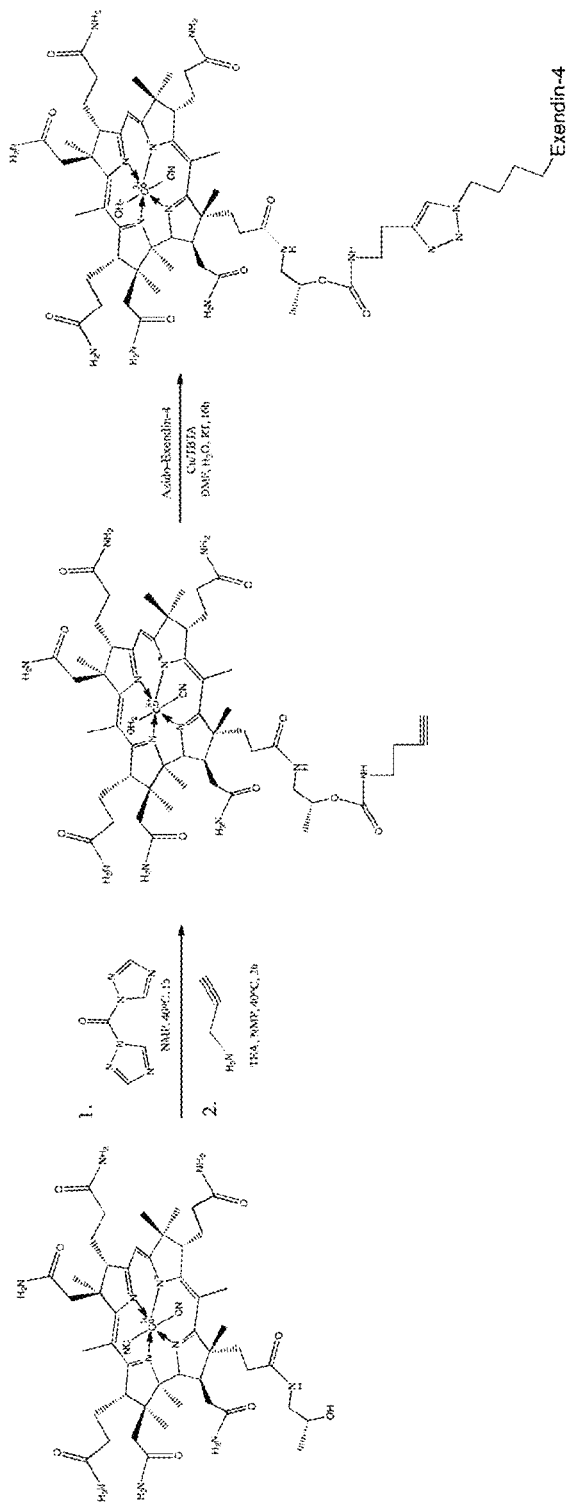
FIG. 20 is a schematic of the synthesis of a cobinamide-exendin 4 conjugate according to the present invention.

Referring to FIG. 20, another exemplary conjugate 10 were formed using Ex-4 as peptide drug 14 and evaluated for the mitigation of side effects. In this Example, a cobinamide (Cbi) was synthesized and conjugated to Ex-4 as seen in FIG. 20. Cbi-Ex4 was synthesized through Huisgen/Sharpless 'Click' Chemistry. Cu(I) (0.01 mmol) and Tris[(1-benzyl-1H-1,2,3-triazol-4-yl)methyl]amine (0.015 mmol) were dissolved in 0.5 mL DMF/H$_2$O (4:1 v/v). Once color change occurred, the peptide exendin-4 and a previously synthesized cobinamide-alkyne conjugate was dissolved and allowed to stir at room temperature overnight.

Figure 21:
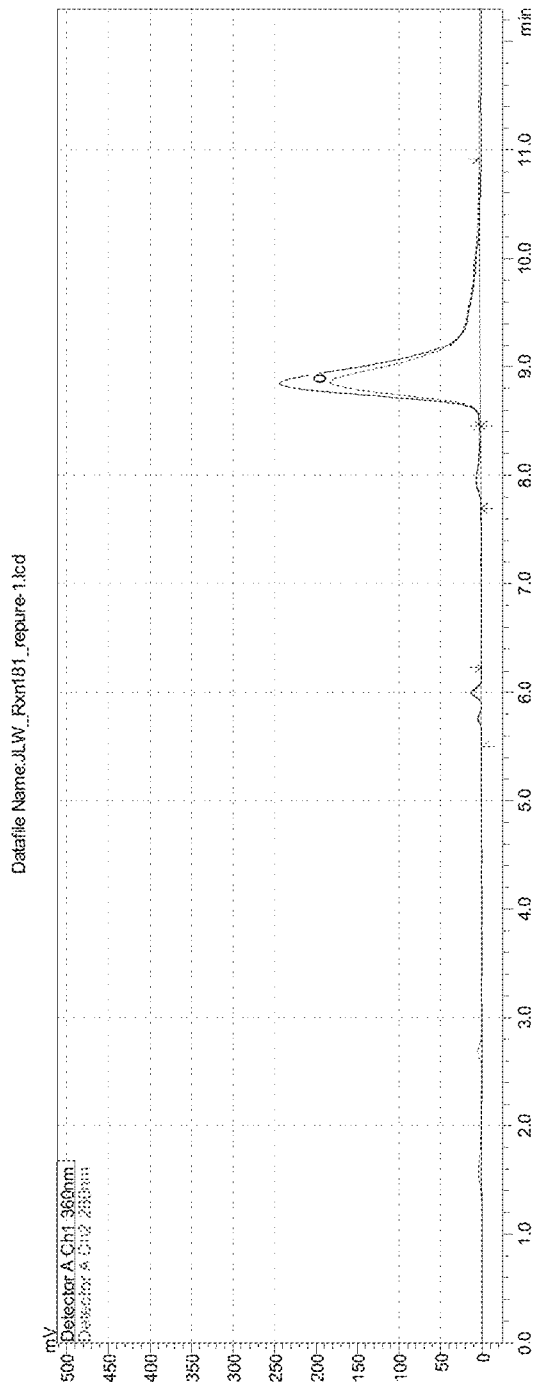
FIG. 21 is a graph of reversed-phase high-performance liquid chromatography (RP-HPLC) performed on the cobinamide-exendin 4 conjugate according to the present invention.
Figure 22:
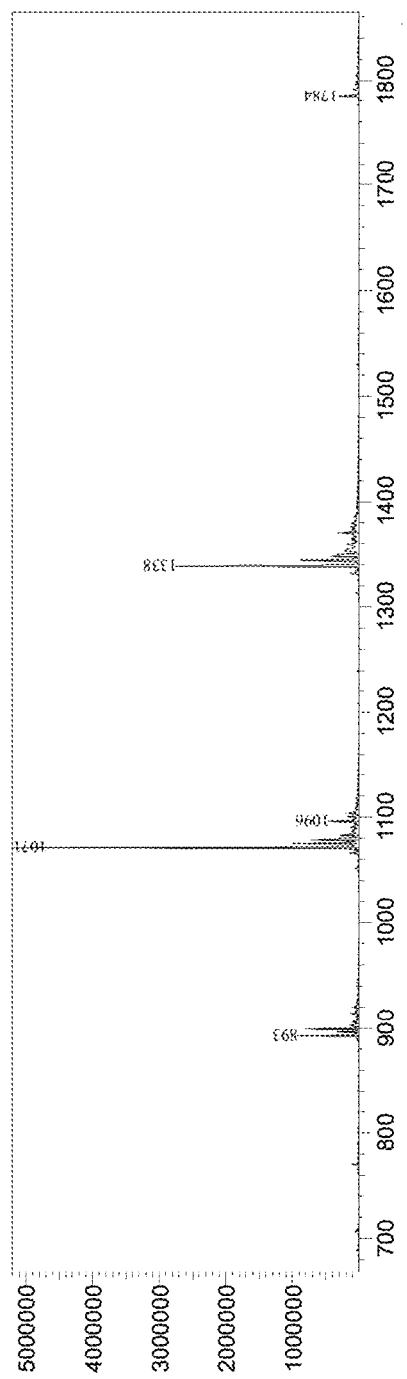
FIG. 22 is a graph of liquid chromatography-mass spectrometry (LC-MS) performed on the cobinamide-exendin 4 conjugate according to the present invention.
Figure 23:
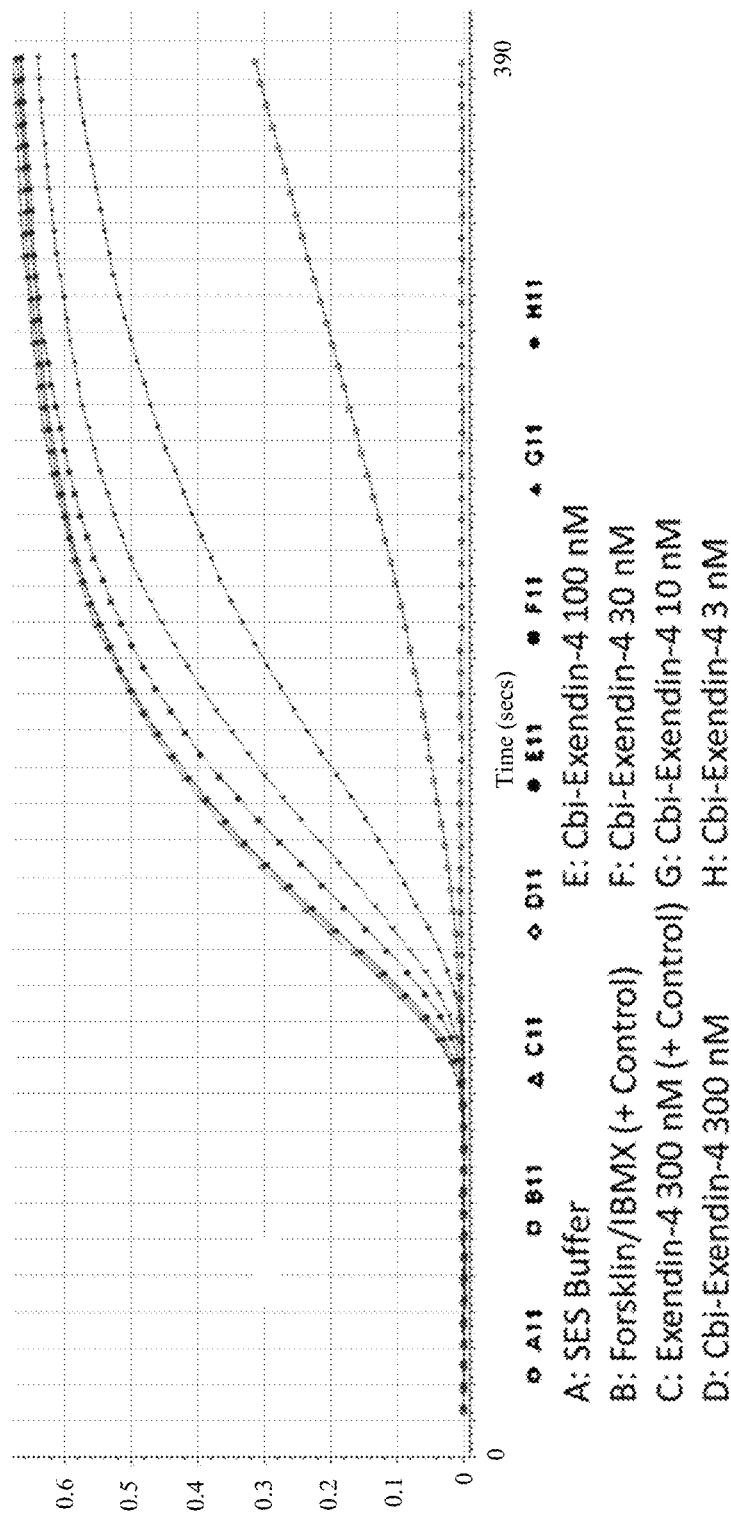
FIG. 23 is a graph of a receptor agonism study at the GLP-1 receptor for the cobinamide-exendin 4 conjugate according to the present invention.
Figure 24:
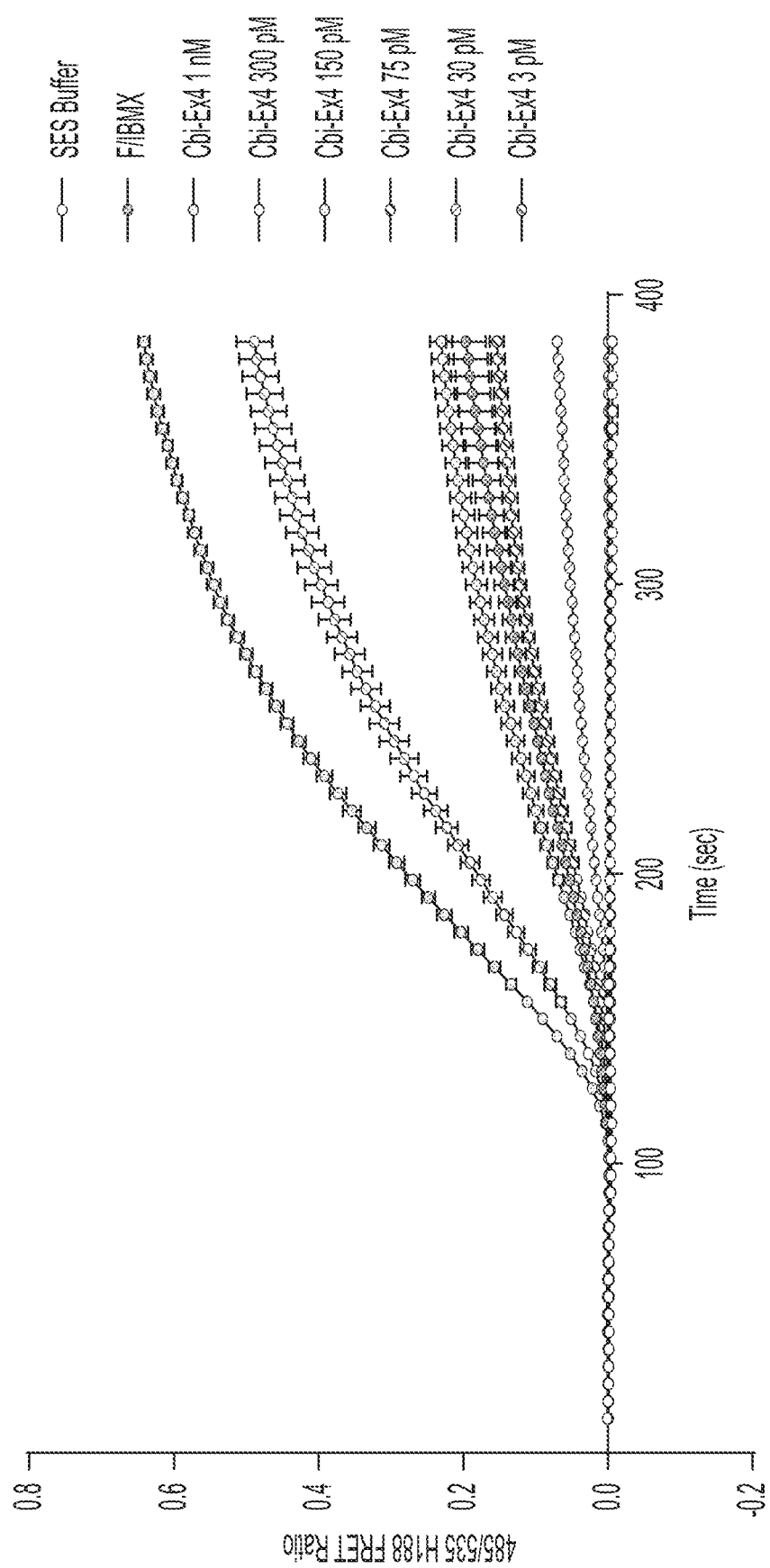
FIG. 24 is a graph of a receptor agonism study at the GLP-1 receptor showing dose response for the cobinamide-exendin 4 conjugate according to the present invention.
Figure 25:
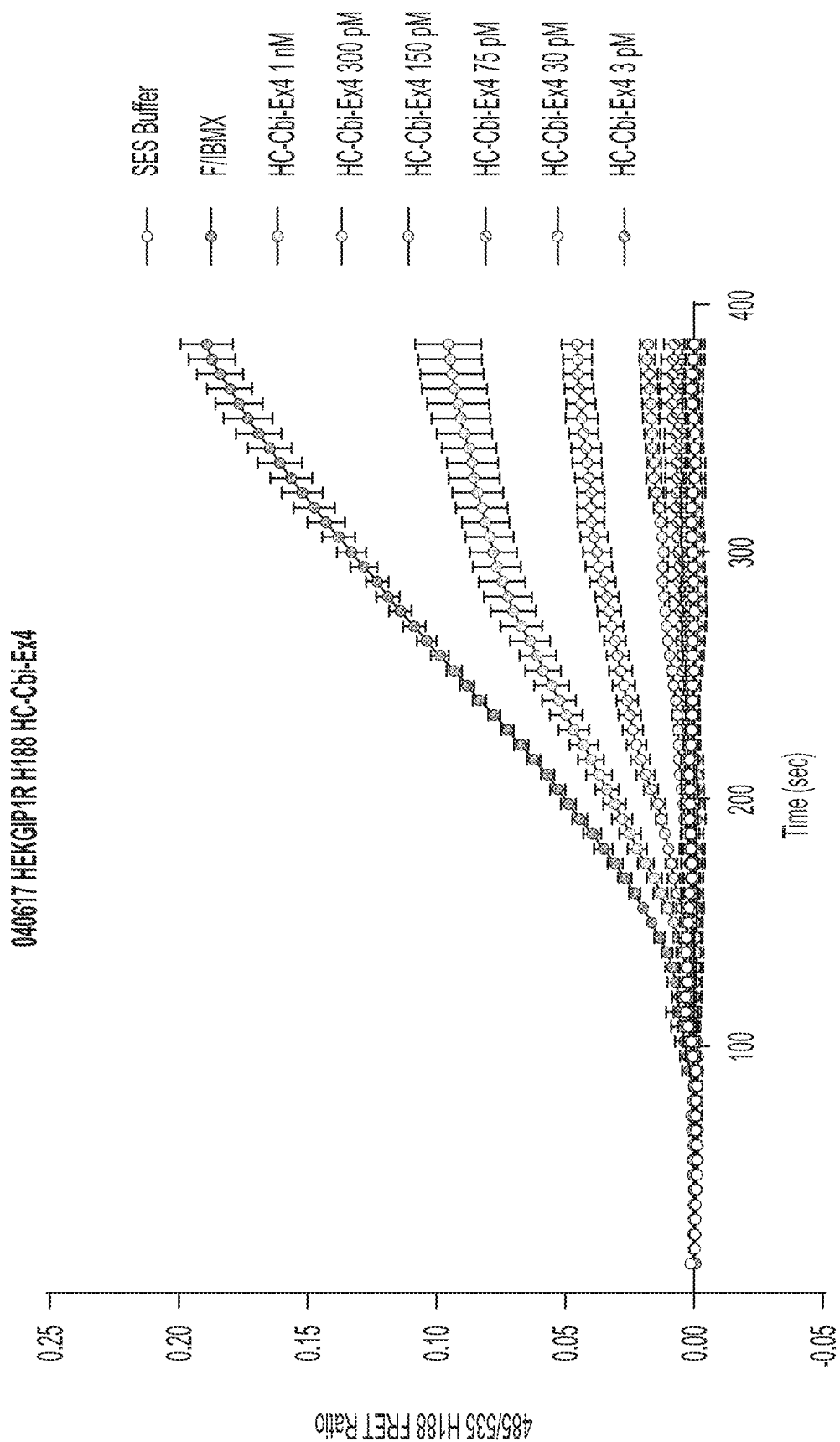
FIG. 25 is a graph of a receptor agonism study at the GLP-1 receptor showing dose response for a cobinamide-exendin 4 conjugate bond to haptocorrin according to the present invention.

The resulting conjugate 10 was assessed using reversed-phase high-performance liquid chromatography (RP-HPLC) and liquid chromatography-mass spectrometry (LC-MS) to confirm the synthesis as seen in FIGS. 21 and 22, respectively. The Cbi-Ex4 conjugate 10 was then tested for agonism at the GLP-1 receptor to verify that conjugate 10 will still function at the target receptor of Ex-4. Agonism at the GLP-1 receptor was achieved by using stably transfected HEK-293 cells with the GLP-1 receptor. Cells were plated on a rat-tail-collagen-coated 96-well plate at 60,000 cell/well and allowed to adhere. Once wells were 75% confluent the cells were infected with the H188 reporter through a virus using a 25 MOI, 3 µL undiluted virus/plate for 16-20 h in 75 µL of DMEM-1% FBS. After the virus incubation the cells were placed in 200 µL standard extracellular matrix with glucose and 0.1% BSA. Conjugates were added to each well at 5× the required concentration. Agonism was determined through a 485/553 nm FRET ratio which indicates a cAMP level increase. As seen in FIG. 23, the use of Cbi in place of B$_{12}$ did not interfere with the activity of Ex-4 used as peptide drug 14 in conjugate 10. Referring to FIGS. 24 and 25, additional testing established that Cbi-Ex-4 conjugate 10 works at the GLP1-R in a dose responsive manner and that, when bound to haptocorrin, will function in nearly an identical matter. In this test, HC and Cbi-Ex4 were mixed to achieve required concentrations in standard extracellular solution at a 1:0.9 ratio, respectively. This solution was allowed to mix overnight at 4° C. The solution was allowed to warm up to room temperature before administration.

Example 4

Critical to the use of haptocorrin targeting substrates, and avoiding transcobalamin II (TCII) binding that could lead to a B$_{12}$ deficiency, is the point that the organism in which the drug is to be used must have haptocorrin only binding (no TCII), or, more likely, both proteins present as separate entities. There are several major concerns about using common murine models for extrapolation to humans in this case. The issue in the use of murine models lies in the fact that humans have two primary B$_{12}$ binding and transport proteins in serum, namely TCII and HC. Mouse serum has a single protein with features of both TCII and HC. Developing systems to prevent TCII binding (by modifying the B$_{12}$ structure) are significantly hampered because the broader specificity of binding inherent in the murine TCII prevents the desired effect from being manifest. In such situations, it is likely that models, such as the rabbit (documented to contain both the serum TCII and HC proteins as in humans) would be a more appropriate choice. Cow, monkey, pig, and have also been documented to contain each of the two serum proteins. Shrews are predicted, through bioinformatic studies, to also contain both proteins, and as mammals and 'pseudo-primates' would make excellent pre-clinical small animal models for study to confirm that the present invention would not bind TCII or result in a B$_{12}$ deficiency.

As an example, a dicyanocobinamide-Exendin-4 conjugate could be administered I.V. in a Chinese tree shrew in a concentration range of 0.5, 1, 5, or 20 µg/kg) after a glucose bolus (1-3 g/Kg D-glucose) IP or orally administered. Blood samples would be taken up to 120 minutes. Controls would be saline vehicle and unmodified Ex-4. The ability of the conjugate to control hyperglycemia could then be compared to Ex-4.

In addition, studies could be conducted to compare the effect of cobinamide conjugation to Ex-4 (as an example) on mitigating nausea and hypophagia. A conditioned taste aversion comparing drugs to Ex-4 and LiCl controls could be conducted to measure nausea, at glucoregulatory concentrations as measured above. A food intake study would likewise be conducted simply measuring food consumption over 3-6 hours at doses ranging as above and using Ex-4 and vehicle as controls.

What is claimed is:

1. A method of providing an improvement to a pharmaceutical effect of a peptide drug, comprising the step of conjugating the peptide drug to an amount of cobinamide so that the peptide drug conjugated to the amount of cobinamide will bind to haptocorrin but not transcobalamin II in serum in the presence of B$_{12}$.

2. The method of claim 1, wherein the peptide drug is Exendin-4.

3. The method of claim 1, wherein the improvement comprises a longer half-life when injected intravenously or subcutaneously.

4. The method of claim 1, wherein the improvement comprises a reduction in central nervous system side effects.

5. The method of claim 4, wherein the reduction in central nervous system side effects is a reduction in nausea.

6. The method of claim 1, wherein the improvement comprises a reduction in weight loss associated with the peptide drug.

7. A compound having improved pharmaceutical effect, comprising a peptide drug and a cobinamide bound to the peptide drug, wherein the cobinamide will bind to haptocorrin but not transcobalamin II in serum in the presence of B$_{12}$.

8. The compound of claim 7, wherein the peptide drug is Exendin-4.

9. The compound of claim 7, wherein the improvement comprises a longer half-life when injected intravenously or subcutaneously.

10. The compound of claim 7, wherein the improvement comprises a reduction in central nervous system side effects associated with the peptide drug.

11. The compound of claim 10, wherein the reduction in central nervous system side effects is a reduction in nausea.

12. The compound of claim 7, wherein the improvement comprises a reduction in weight loss associated with the peptide drug.

* * * * *